(12) United States Patent
Tamrazi et al.

(10) Patent No.: US 10,556,058 B2
(45) Date of Patent: Feb. 11, 2020

(54) APPARATUS FOR SECURELY AND GENTLY HOLDING A FLEXIBLE ELONGATED MEDICAL DEVICE

(71) Applicant: CATH LAB SOLUTIONS LLC, Redwood City, CA (US)

(72) Inventors: Anobel Tamrazi, Redwood City, CA (US); Patricia Judge Tamrazi, Redwood City, CA (US)

(73) Assignee: Cath Lab Solutions LLC, Redwood City, CA (US)

( * ) Notice: Subject to any disclaimer, the term of this patent is extended or adjusted under 35 U.S.C. 154(b) by 2 days.

(21) Appl. No.: 15/551,662

(22) PCT Filed: Feb. 17, 2016

(86) PCT No.: PCT/US2016/018169
§ 371 (c)(1),
(2) Date: Aug. 17, 2017

(87) PCT Pub. No.: WO2016/133962
PCT Pub. Date: Aug. 25, 2016

(65) Prior Publication Data
US 2018/0021507 A1    Jan. 25, 2018

Related U.S. Application Data

(60) Provisional application No. 62/117,786, filed on Feb. 18, 2015.

(51) Int. Cl.
*A61M 25/02* (2006.01)
*A61M 5/14* (2006.01)

(52) U.S. Cl.
CPC .......... *A61M 5/1418* (2013.01); *A61M 25/02* (2013.01); *A61M 2025/024* (2013.01); *Y10T 24/44444* (2015.01); *Y10T 24/44564* (2015.01)

(58) Field of Classification Search
CPC ............... Y10T 24/44932; Y10T 24/44; Y10T 24/44154; Y10T 24/44444;
(Continued)

(56) References Cited

U.S. PATENT DOCUMENTS 2,268,407 A   12/1941   Krone et al.
2,715,731 A    8/1955   Paul
(Continued)

FOREIGN PATENT DOCUMENTS

CN   201042440 Y   4/2008
EP     0782868 A1   7/1997
(Continued)

OTHER PUBLICATIONS

Marian_ 3 questions answered about compression set resistance in foams; 4 pages; retrieved from the internet (http://blog.marianinc.com/blog/3-questions-answered-about-compression-set-resistance-in-foams) on Aug. 24, 2018.
(Continued)

*Primary Examiner* — Robert Sandy
*Assistant Examiner* — Michael S Lee
(74) *Attorney, Agent, or Firm* — Fish & Richardson P.C.

(57) ABSTRACT

A clip for holding a flexible elongated medical device. In embodiments, the clip has a hinge; first and second jaws movable with respect to each other about the hinge from a closed position to an open position, each of the jaws having a contact surface, the contact surface of the first jaw being disposed against the contact surface of the second jaw when the clip is in the closed position and away from the contact surface of the second jaw when the clip is in the open position; and flexible material disposed on at least one of the jaws, the flexible material comprising the contact surface. The invention also includes methods of holding a flexible elongated medical device.

17 Claims, 11 Drawing Sheets

(58) Field of Classification Search
CPC ......... Y10T 24/44564; Y10T 24/44769; Y10T 24/44778; Y10T 24/44786; A61M 5/1418; A61M 2025/024
See application file for complete search history.

(56) References Cited

U.S. PATENT DOCUMENTS

| | | | |
|---|---|---|---|
| 3,382,545 A | 5/1968 | Spenner | |
| 3,616,497 A | 11/1971 | Esposito | |
| 3,636,595 A | 1/1972 | Wines | |
| 4,200,249 A | 4/1980 | Synstelien et al. | |
| 4,277,864 A | 7/1981 | Orson | |
| 4,390,019 A | 6/1983 | LeVeen et al. | |
| 4,406,042 A | 9/1983 | McPhee | |
| 4,407,472 A | 10/1983 | Beck | |
| 4,607,746 A | 8/1986 | Stinnette | |
| 4,829,999 A | 5/1989 | Auth | |
| 4,838,880 A | 6/1989 | Honma | |
| 4,896,465 A | 1/1990 | Rhodes et al. | |
| 4,897,082 A | 1/1990 | Erskine | |
| 4,903,826 A | 2/1990 | Pearce | |
| 5,027,478 A | 7/1991 | Suhr | |
| D323,588 S | 2/1992 | Pelosi | |
| 5,125,416 A | 6/1992 | Phillips | |
| 5,226,892 A | 7/1993 | Boswell | |
| 5,309,704 A | 5/1994 | Grando | |
| 5,364,355 A | 11/1994 | Alden et al. | |
| 5,366,444 A | 11/1994 | Martin | |
| 5,372,592 A | 12/1994 | Gambale | |
| 5,392,918 A | 2/1995 | Harrison | |
| 5,407,071 A | 4/1995 | Lawhon et al. | |
| 5,454,785 A | 10/1995 | Smith | |
| 5,560,138 A | 10/1996 | Dentsbier | |
| 5,730,150 A | 3/1998 | Peppel et al. | |
| 5,735,821 A | 4/1998 | Dobkin | |
| 5,738,213 A | 4/1998 | Whiting et al. | |
| 5,769,222 A | 6/1998 | Banerian | |
| 5,769,786 A | 6/1998 | Wiegel | |
| 5,815,894 A | 10/1998 | Soriano | |
| 5,830,183 A | 11/1998 | Krieger | |
| 5,843,002 A | 12/1998 | Pecor et al. | |
| 5,871,189 A | 2/1999 | Hoftman | |
| 5,978,699 A | 11/1999 | Fehse et al. | |
| 6,047,825 A | 4/2000 | Samuels | |
| 6,086,008 A | 7/2000 | Gray et al. | |
| 6,231,564 B1 | 5/2001 | Gambale | |
| 6,375,006 B1 | 4/2002 | Samuels | |
| 6,393,675 B1 * | 5/2002 | Gaetke | B65D 35/18 222/92 |
| 6,405,414 B1 | 6/2002 | Byrnes et al. | |
| 6,460,231 B2 | 10/2002 | Bourgerie | |
| 6,547,072 B2 | 4/2003 | Whiting et al. | |
| 6,569,106 B1 | 5/2003 | Ullman | |
| 6,588,588 B2 | 7/2003 | Samuels | |
| 6,691,946 B2 | 2/2004 | Dannecker et al. | |
| 6,804,866 B2 | 10/2004 | Lemke et al. | |
| D522,850 S | 6/2006 | Mandel | |
| 7,062,822 B2 | 6/2006 | Folkmar | |
| 7,191,900 B2 | 3/2007 | Opie et al. | |
| 7,490,722 B2 | 2/2009 | Mayda et al. | |
| 7,494,010 B2 | 2/2009 | Opie et al. | |
| 7,524,309 B2 | 4/2009 | McConnell et al. | |
| 7,559,125 B2 | 7/2009 | Cofer | |
| 7,766,162 B2 | 8/2010 | Mäki et al. | |
| 7,886,906 B1 | 2/2011 | Dunn | |
| 7,951,092 B2 | 5/2011 | Jones et al. | |
| 7,963,947 B2 | 6/2011 | Kurth et al. | |
| 8,277,417 B2 | 10/2012 | Fedinec | |
| D676,315 S | 2/2013 | Widdison | |
| 8,454,635 B2 | 6/2013 | Paolitto et al. | |
| 8,556,884 B2 | 10/2013 | Hong et al. | |
| 8,594,478 B2 | 11/2013 | Seftel et al. | |
| 8,672,124 B2 | 3/2014 | Burgess et al. | |
| 9,127,786 B1 | 9/2015 | Aratia | |
| 9,499,318 B2 | 11/2016 | Mohika | |
| 9,664,213 B2 | 5/2017 | Mohika et al. | |
| 10,280,955 B2 * | 5/2019 | Mohika | F16B 2/22 |
| 2002/0007538 A1 * | 1/2002 | Bourgerie | A01K 97/08 24/517 |
| 2003/0171759 A1 | 9/2003 | Sadler et al. | |
| 2005/0178684 A1 | 8/2005 | Kesler et al. | |
| 2005/0184187 A1 | 8/2005 | Ullman et al. | |
| 2006/0094987 A1 | 5/2006 | van Erp et al. | |
| 2006/0249635 A1 | 11/2006 | Newkirk et al. | |
| 2006/0272135 A1 | 12/2006 | Alitowski | |
| 2008/0319387 A1 | 12/2008 | Amisar et al. | |
| 2009/0076417 A1 | 3/2009 | Jones | |
| 2010/0006738 A1 | 1/2010 | Teirstein | |
| 2010/0010475 A1 | 1/2010 | Teirstein et al. | |
| 2010/0115739 A1 * | 5/2010 | Mathur | A45F 5/02 24/306 |
| 2010/0152613 A1 | 6/2010 | Ryan et al. | |
| 2010/0305474 A1 | 12/2010 | DeMars et al. | |
| 2010/0307496 A1 | 12/2010 | Lueckenhoff | |
| 2011/0087171 A1 | 4/2011 | Bracci | |
| 2011/0127186 A1 | 6/2011 | Enns et al. | |
| 2013/0020426 A1 | 1/2013 | Abri et al. | |
| 2013/0086773 A1 | 4/2013 | Cude | |
| 2013/0184659 A1 | 7/2013 | Byrnes et al. | |
| 2014/0171833 A1 | 6/2014 | Matsuno et al. | |
| 2016/0053784 A1 * | 2/2016 | Mohika | F16B 2/10 24/132 R |
| 2018/0021507 A1 | 1/2018 | Tamrazi et al. | |

FOREIGN PATENT DOCUMENTS

| | | |
|---|---|---|
| EP | 0801955 B1 | 3/1999 |
| EP | 1551715 B1 | 9/2009 |
| FR | 1534122 A | 7/1968 |
| WO | WO96/02294 A1 | 2/1996 |
| WO | WO98/56687 A1 | 12/1998 |

OTHER PUBLICATIONS

Stockwell Elastomerics Inc.; Compression set of elastomeric materials; 8 pages; retrieved from the interent (https://www.stockwell.com/compression-set-testing/) on Aug. 24, 2018.

Tsaii et al.; The compressive deformation of polymeric foams; Polymer Engineering and Science; 22(9); pp. 545-548; (Abstract Only) Jun. 1982.

Wikipedia; Compression set; 1 page retrieved from the internet (https://en.wikipedia.org/wiki/Compression_set) on Aug. 24, 2018.

Wikipedia; Deformation; 8 page; retrieved from the internet (https://en.wikipedia.org/wiki/Deformation_(engineering)) on Aug. 24, 2018.

* cited by examiner

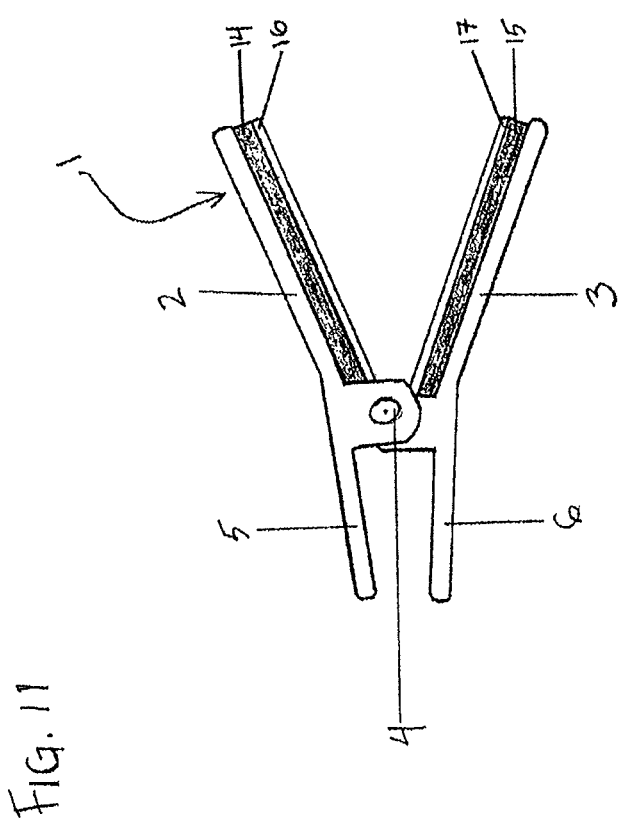

APPARATUS FOR SECURELY AND GENTLY HOLDING A FLEXIBLE ELONGATED MEDICAL DEVICE

CROSS REFERENCE TO RELATED APPLICATIONS

This application claims the benefit of U.S. application Ser. No. 62/117,786, filed Feb. 18, 2015, the disclosure of which is incorporated herein by reference.

INCORPORATION BY REFERENCE

All publications and patent applications mentioned in this specification are incorporated herein by reference in their entirety to the same extent as if each individual publication or patent application was specifically and individually indicated to be incorporated by reference.

TECHNICAL FIELD OF THE INVENTION

The present invention relates to medical devices in general, and in particular to a device for securely and gently holding a flexible elongated medical device, such as a catheter or guide wire, in between uses during a medical procedure. The present invention also has non-medical uses, such as securely and gently holding fiber optic cables, other types of cables, hoses, jewelry (such as necklaces or bracelets), and similar flexible elongated items.

BACKGROUND

As an alternative to invasive-type surgeries whereby a physician creates an incision to access a desired location in the patient's body, many minimally invasive medical procedures are being performed using flexible elongated medical devices that are inserted into a patient's body. These flexible elongated medical devices include guide wires, catheters, flexible stents, tubing, wires, fiber optic equipment, drains, balloons, and so forth. Due to their nature, these flexible elongated medical devices can be awkward to handle, organize, and store, and there is currently no effective way to securely and gently hold a flexible elongated medical device in between uses during a medical procedure.

An example will be illustrative of the context in which there is a need for this invention. Certain minimally invasive medical procedures involve the insertion of a catheter into the human body. In order to insert a catheter into the appropriate portion of the body, which will be a tubular structure of interest such as an artery, a guide wire for the catheter must first be inserted. Initially, a needle is used to enter the body, through the patient's skin and into the tubular structure of interest. A guide wire is then inserted through the needle and into the body, after which the needle is removed. The guide wire is pushed through the tubular structure of interest, and once the guide wire is positioned in the desired location, another flexible elongated medical device, such as a catheter, may be inserted over the guide wire, the guide wire thereby "guiding" the other flexible elongated medical device in use into the appropriate position in the tubular structure inside the patient's body. Once the flexible elongated medical device is in place, the guide wire is then removed or exchanged so that the next step in the desired medical procedure may be performed, such as obtaining a biological sample, delivering an agent, or deploying a medical device such as a stent.

Flexible elongated medical devices, such as guide wires and catheters, are of various lengths, calibers, stiffnesses, and materials, depending on the use for which they are intended. Because of their different properties, several different flexible elongated medical devices are used during a single procedure, and many of those individual flexible elongated medical devices are used and reused during a single procedure. While in use during a procedure, a flexible elongated medical device is removed from its sterile packaging and is inserted into the patient, with a portion of the flexible elongated medical device remaining outside of the patient's body such that the flexible elongated medical device can be removed. The flexible elongated medical devices are often two (2) meters long and have a natural tendency to remain straight. Problems arise in finding a means for securely and gently holding, and maintaining the sterility of, flexible elongated medical devices when they are outside of the patient's body within the sterile procedural field and in between uses during a single procedure.

At the present time, the handling and management of flexible elongated medical devices outside of the patient's body during a procedure is both awkward and inefficient. To be managed, a flexible elongated medical device that is removed from the patient's body after use but which may be used again in the same procedure is looped around itself by hand, as would be an extension cord, so that it is in a coiled condition. The portion of the flexible elongated medical device held in a coiled condition is then discouraged from springing into its naturally straight configuration in a number make-shift of ways, such as (a) by placing the coiled flexible elongated medical device in a bowl and allowing it to push out against the sides of the bowl (which can be especially messy when using multiple flexible elongated medical devices, as a number of flexible elongated medical devices may accumulate in the bowl, making it difficult to locate a specific device and remove it from the bowl for use when needed during the procedure without tangling with other flexible elongated medical devices or dislodging other flexible elongated medical devices from the bowl), (b) by winding the loose end of the flexible elongated medical device around the coiled portion (which can be difficult to control), and/or (c) by placing a weighted object, such as a sterile towel, on the coiled portion to prevent it from uncoiling or springing open (which can be difficult to control and bulky, with towels or other weighted objects lying on the operative field). The flexible elongated medical device that is coiled and discouraged from springing into its naturally straight configuration is put aside by the technician within the sterile procedural field when not in use so that another flexible elongated medical device may be used; it is likely that the flexible elongated medical device that is coiled and discouraged from springing into its naturally straight configuration may be used again during the same procedure. Before reuse, the technician may need to ensure that the flexible elongated medical device is moist or wiped clean, depending on the particular flexible elongated medical device being reused and its particular use.

The make-shift ways of discouraging coiled flexible elongated medical devices from springing into straight configurations are unstable and unreliable. As stated previously, the natural state of a flexible elongated medical device is for it to be straight, so it is resistant to passive coiling. When it is looped in a coiled condition, which is how these devices are managed during procedures, potential energy is stored in the coiled condition much like potential energy is stored in a spring. These devices have a tendency to expand outwardly in a radial manner, pushing to be straight, and they can "spring open" unintentionally if not prevented from doing so. There is currently no way to reliably hold these devices in place while not in use.

Inefficiencies, inconvenience, waste, and increased cost therefore result from these make-shift techniques of managing flexible elongated medical devices during procedures. It can take time for a technician to secure a flexible elongated medical device in between the device's uses with these make-shift techniques, as they need to be adjusted just right to hold the device that is pushing to be straight. These techniques can be burdensome and can add time to the procedure. Further, a flexible elongated medical device stored outside of the patient's body during a procedure in this unstable way can spring open and become unacceptably contaminated or otherwise damaged by falling onto the floor or coming into contact with an unsterile surface in between uses, thereby compromising sterility or function. When this happens, time must be taken to thoroughly clean the contaminated flexible elongated medical device for reuse or the flexible elongated medical device may need to be discarded (whether due to contamination or damage) and replaced with an identical device immediately rather than being able to be reused, causing unnecessary delay as the medical team must search for a new replacement device and prepare such a device for use. Replacement of accidentally contaminated or damaged flexible elongated medical devices can add to the expense of a medical procedure by increasing the cost of materials and procedure time. Additionally, delay while searching for a new flexible elongated medical device at a critical point during a procedure may place a patient's life and/or health at risk and increase the potential liability for medical personnel if something goes wrong during the procedure. Further, the mess and inconvenience of having no efficient way to securely and gently hold flexible elongated medical devices during procedures can be distracting and add to procedure time, thereby increasing cost.

The current invention solves these problems by providing an apparatus which may be used to securely and gently hold a flexible elongated medical device between uses during a medical procedure in a reliable, compact, and efficient way.

The foregoing objects and advantages of the invention are illustrative of those that can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variation which may be apparent to those skilled in the art. Accordingly, the present invention resides in the novel methods, arrangements, combinations, and improvements herein shown and described.

SUMMARY OF THE DISCLOSURE

The present invention provides a device which overcomes all of the above-mentioned disadvantages of the previously-known methods of holding, controlling, organizing, and storing a flexible elongated medical device between uses during a minimally invasive procedure. A brief summary of the present invention is presented. Some simplifications and omissions may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

One aspect of the invention provides a clip for holding a coiled flexible elongated medical device. In some embodiments, the clip has a hinge; first and second jaws movable with respect to each other about the hinge from a closed position to an open position, each of the jaws having a contact surface, the contact surface of the first jaw being disposed against the contact surface of the second jaw when the clip is in the closed position and away from the contact surface of the second jaw when the clip is in the open position; and flexible material disposed on at least one of the jaws, the flexible material comprising the contact surface. By "hinge," we mean a point or bend between two elements (e.g., the jaws of the clip disclosed herein) that permits the two elements to move with respect to each other, such as a door hinge, pivot, living hinge, cantilever, or fold. A "hinge" can be separate from the two elements that move with respect to each other, such as with a door hinge. A "hinge" can be part of one piece contiguous with the two elements that move with respect to each other, with or without any difference in material or deformity in that contiguous piece that allows for the pivot or bend, visible or not, such as with a living hinge or fold in a paper clip, bobby pin, binder clip, or the like; in such an embodiment, the first jaw, the second jaw, and the hinge may be all one piece, such as made of a molded plastic or bent metal. The hinge may be further adapted to exert a force between the contact surfaces to hold the flexible elongated medical device in its coiled configuration without damaging the device. In some embodiments, the clip also has a spring biasing the hinge to urge the jaws toward the closed position. In some embodiments of the clip, the hinge may be a living hinge, optionally a living hinge that is also a spring. The clip may also have first and second handles extending from the first and second jaws, respectively, to move the clip between the closed and open positions.

In some embodiments, at least one of the jaws has an extension portion extending toward the other jaw, the extension portion contacting the other jaw when the clip is in the closed position.

In some embodiments, the hinge is a living hinge that does not bias the clip toward the closed position. The clip may also have a latch adapted to maintain the clip in the closed position. In some embodiments, the latch may be further adapted to apply a force to the jaws during actuation of the latch.

Some embodiments may have a cleaning material disposed over the flexible material, the cleaning material comprising the contact surface. Some embodiments may have a textured surface on the flexible material, the textured material comprising the contact surface. The flexible material may optionally have a lubricious surface. The flexible material may optionally be a material which soaks up and holds liquid.

Another aspect of the invention provides a method of holding a flexible elongated medical device. Some embodiments include the steps of opening a clip; inserting proximal and distal portions of the flexible elongated medical device between opposing contact surfaces of the clip, the flexible elongated medical device being arranged in at least one coil; and closing the clip to grasp the flexible elongated medical device between the contact surfaces; at least one of the contact surfaces comprising a flexible material.

Some embodiments add the step of coiling the flexible elongated medical device prior to the inserting step. The method may also include the step of opening the clip to remove the flexible elongated medical device.

In some embodiments, the opening step includes the step of moving the first and second jaws against the action of a spring or living hinge biasing the clip toward the closed position. Such embodiments may also include the step of permitting the spring or living hinge to move the first and second jaws toward each other. In some embodiments, force from the spring or living hinge holds the flexible elongated medical device between the contact surfaces. The method may also include the step of latching the clip after the closing step to, e.g., apply a force between the contact surfaces to hold the flexible elongated medical device.

In some embodiments, at least one of the contact surfaces may have a cleaning material. In such embodiments, the method may also include the step of engaging the flexible elongated medical device with the cleaning material.

Embodiments of the present invention provide a clip apparatus configured to securely and gently hold a flexible elongated medical device. In some embodiments, the clip is comprised of an upper jaw and a lower jaw, each of them having a grasping part on the internal plane of the jaw. The jaws are articulated with respect to one other about a hinge between a closed position and an open position. The hinge portion hingeably mounts the top jaw to the bottom jaw for clamshell movement of the respective jaws between the closed position and the open position. The clip further includes a means for moving the jaws between said closed position and said open position using handles or other holding features attached to both jaws, enabling manual operation between the closed position and the open position. When the clip is in the open position, a flexible elongated medical device may be inserted in the clip's longitudinal opening. When the clip is in the closed position, the internal planes of the jaws meet, acting to frictionally grip the flexible elongated medical device without being held by the user. Therefore, a flexible elongated medical device may be mounted between said jaws when the jaws are in an open position, so that the flexible elongated medical device is securely and gently held without assistance of the user when the jaws are closed and can be removed when the jaws are open.

In one embodiment, the hinge portion is a spring hinge or living hinge biasing the jaws into the closed position. In this embodiment, one end of the clip contains a grasping part to hold a flexible elongated medical device, and the opposite end of the clip contains the handles configured for clamshell movement of the respective jaws between the closed position and the open position, with a hinge in between the two ends. Force applied to the handles causes the jaws to open; when such force is removed from the handles, the jaws close. A flexible elongated medical device can be held between the internal planes of the jaws of the clip when the clip is in the closed position. The portion of the jaws of the clip which hold a flexible elongated medical device are flat in the preferred embodiment. In an alternative embodiment, one or both tips of the portion of the jaws of the clip which hold a flexible elongated medical device are bent toward each other to hold the tension from the clip's hinge at the tip of the jaws.

In an alternative embodiment, the hinge portion is a living hinge that does not bias the clip toward the closed position. In this embodiment, the user puts his hand in holding features that help him to grip the jaws to move the jaws between the closed position and the open position. When the clip is in the closed position, a coupling feature can be used to latch the jaws together to keep the clip in the closed position and retain a flexible elongated medical device when the user is not holding the clip by, e.g., applying a force between the contact surfaces to hold the flexible elongated medical device. To move the clip from the latched closed position to the open position, the user can unhook the coupling feature and use the holding features to open the jaws.

The grasping part of the internal planes of the jaws of the clip can take various forms. One or both internal planes of the jaws of the clip can be covered with a flexible material, such as thin metal, flexible plastic, silicone, durometer of 70-80 A, polypropylene, a firm open cell foam, or a silicone foam, to help softly grip the flexible elongated medical device held by the clip; this flexible material can be an absorptive material, such as a foam material, cloth, sponge, or gauze, which may be wet before the clip is used to prevent the clip from sticking to the flexible elongated medical device held by the clip due to adherent blood and, when using the clip to securely and gently hold a flexible elongated medical device with a hydrophilic coating, the clip with the wet absorptive material can be moved over the device with a hydrophilic coating to keep it moist. One or both internal planes of the jaws of the clip which touch the flexible elongated medical device being held by the clip can be covered with a cleaning material such as gauze, another textile from cotton or polyester, or Telfa so that the flexible elongated medical device held by the clip may be wiped clean of adherent blood. One or both internal planes of the jaws of the clip which touch the flexible elongated medical device being held by the clip can be textured, such as by using a molding polymer or a textured textile or foam, to help grip the flexible elongated medical device held by the clip, yet that texture cannot have so much grit as to damage the flexible elongated medical device held by the clip.

When in a closed position and holding a flexible elongated medical device, the pressure placed by the clip on the flexible elongated medical device is between the least pressure needed to hold the flexible elongated medical device in a coiled condition that has the most potential energy when in a coiled condition and the most pressure allowed before damaging the most fragile flexible elongated medical device when such device is held by the clip such that this flexible elongated medical device is retained in the clip.

The clip is a size that a typical user can easily operate with only one hand and that does not take too much space when placed on the sterile field or in the bowl filled with saline commonly used during a minimally invasive procedure.

The part of the clip comprising the jaws is made of a firm material, which can take various forms. In the preferred embodiment, the jaws are made of a material that is disposable and single-use, such as a thermoplastic like polyethylene, polypropylene, polystyrene, PVC, or PMMA or an elastometer like silicone; alternative disposable and single-use materials include metal, silicone rubber, nitinol, ABS, polycarbonate, nylon, or polyurethane. In an alternative embodiment, the jaws are made of metal which can be sterilized, in which case any material covering the grasping part of the internal planes of the jaws, if included in the embodiment and not able to be sterilized for reuse in the same way as the metal, will be removable and disposable, designed to be used on only one patient.

The parts of the clip held by the user to control the jaws of the clip can take various forms. For example, to help the user hold onto the clip, the parts of the clip held by the user may have a ridged surface, a rubber surface, or holes or indentations where the user's fingers can grip the clip.

The clip can have a labeling feature to help the user to identify which flexible elongated medical device is being held by the clip. This feature can be on the outward-facing planes of the jaws and, for example, can be a stick-on type label, a surface adapted to be written on, or a color on the surface of the clip easily visible to the user.

The part of the clip that holds a flexible elongated medical device can take various shapes. For example, it can be square, rectangular, oval, crescent, or some other shape.

BRIEF DESCRIPTION OF THE DRAWINGS

In order to better understand the present invention, reference is made to the accompanying drawings, in which similar reference characters refer to similar parts, and in which:

FIG. 11 is a side view of the clip shown in FIG. 10, where the clip is in an open position.

Figure 1:
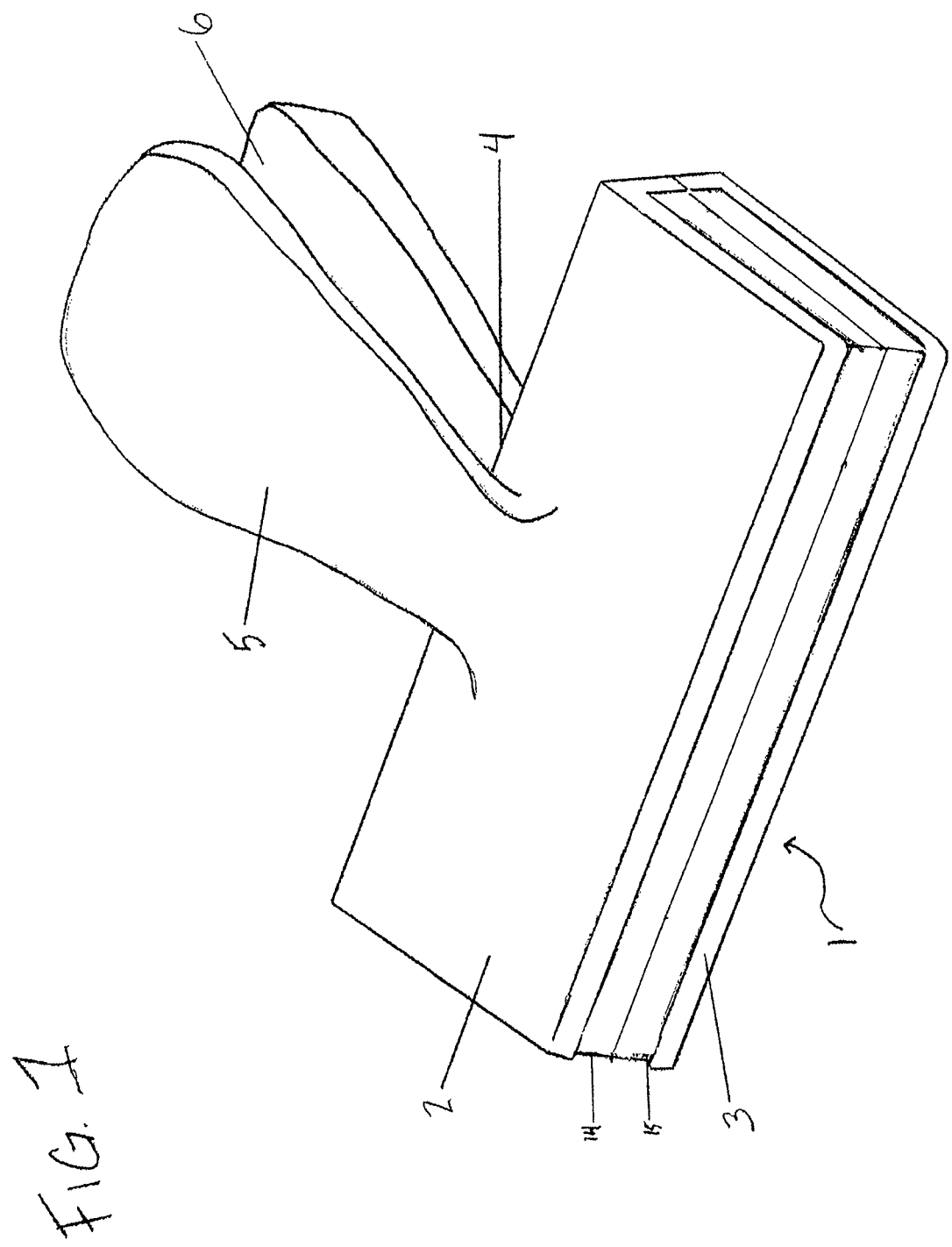
FIG. 1 is a perspective view of a clip according to one embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help improve understanding of embodiments of the present invention.

DETAILED DESCRIPTION

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 2:
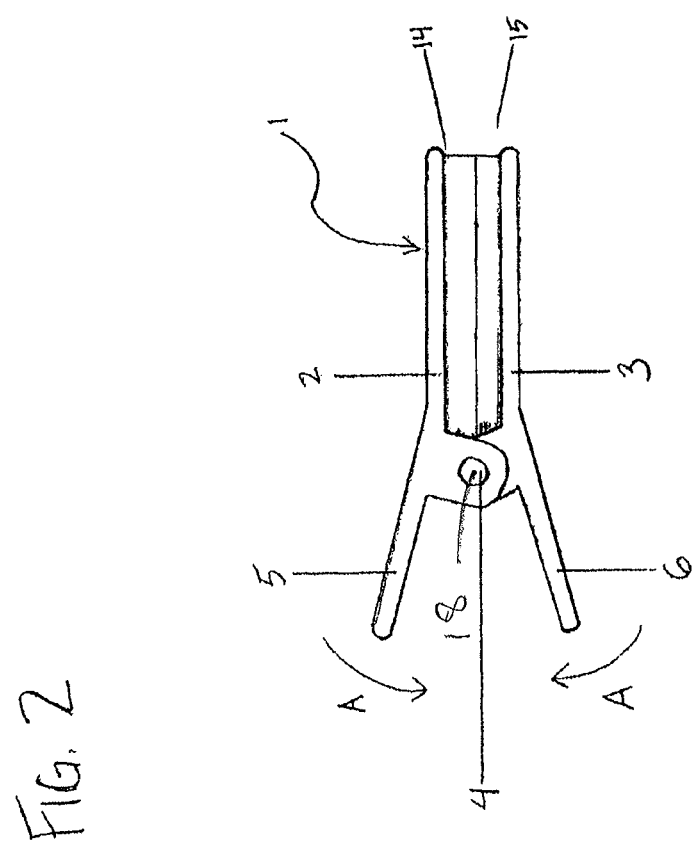
FIG. 2 is a side view of the clip shown in FIG. 1, where the clip is in a closed position.
Figure 3:
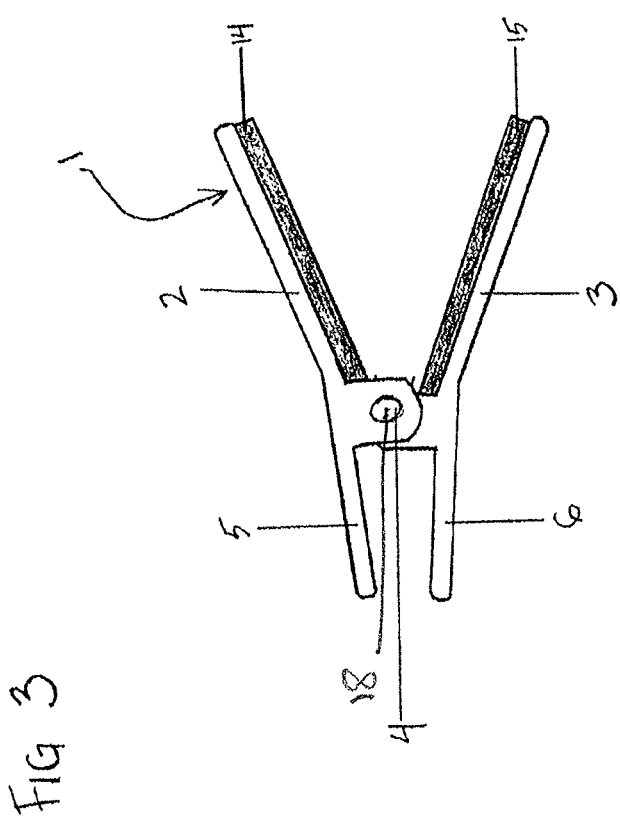
FIG. 3 is a side view of the clip shown in FIG. 1, where the clip is in an open position.
Figure 4:
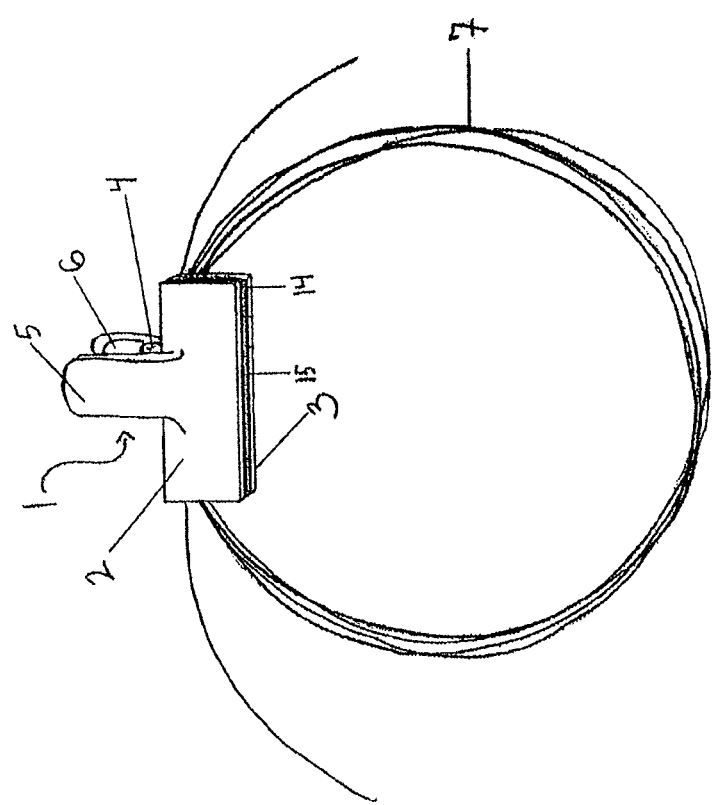
FIG. 4 is a perspective view of the clip shown in FIG. 1 holding a coiled flexible elongated medical device.

FIG. 1 shows a clip 1 according to one embodiment of the invention. The clip 1 has an upper jaw 2 and a lower jaw 3. The jaws 2 and 3 are articulated about a hinge 4, allowing them to be moved between a closed position, as seen in FIG. 2, and an open position, as seen in FIG. 3. The upper jaw 2 has a handle 5 and the lower jaw 3 has a handle 6. As shown in FIGS. 2 and 3, moving the handles 5 and 6 toward each other in the direction of the arrows A in FIG. 2 causes the clip to open. The hinge 4 may be, e.g., a spring hinge that causes the jaws 2 and 3 to be biased into a closed position. The spring force of the spring must be sufficient to hold between the jaws the flexible elongated medical device in a coiled condition that has the most potential energy when in a coiled condition (i.e., the condition in which the coiled medical device has the highest potential energy due to, e.g., spring forces of the medical device resisting the coiling) but not so strong as to damage the most fragile flexible elongated medical device when held between the jaws. Spring hinge 4 may include, e.g., a torsion spring that tightens when handles 5 and 6 move toward each other about a pivot 18. When the handles 5 and 6 are pressed together in the direction of arrows A in FIG. 2, tension is placed on the spring hinge 4, and the jaws 2 and 3 open as illustrated in FIG. 3. Releasing the handles 5 and 6 relieves the tension on the spring hinge 4, and the spring hinge 4 urges the jaws 2 and 3 into a closed position. A flexible elongated medical device 7 may be placed between the jaws 2 and 3 through the longitudinal opening when the jaws 2 and 3 are open. When the handles 5 and 6 are released, the spring hinge 4 will urge jaws 2 and 3 toward each other to hold the flexible elongated medical device 7 between them, as illustrated by FIG. 4. When the user desires to remove the flexible elongated medical device 7 from the clip 1, the user can pick up the clip 1 in the closed position and holding the flexible elongated medical device 7 as illustrated by FIG. 4, press the handles 5 and 6 together, placing tension on the spring hinge 4 so that the jaws 2 and 3 open, and remove the flexible elongated medical device 7 from the clip 1 through the longitudinal opening.

In an alternative embodiment, the spring hinge and pivot of the previous embodiment may be replaced with a living hinge providing a spring force.

Figure 5:
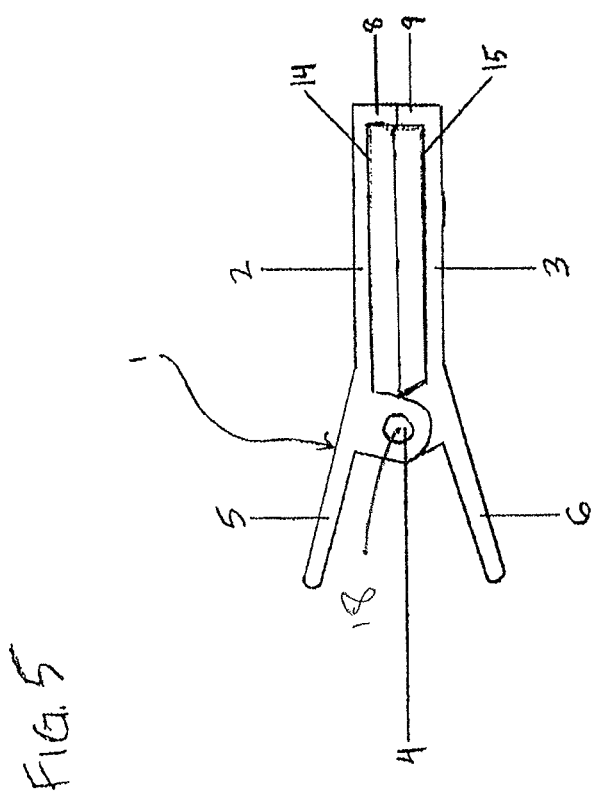
FIG. 5 is a side view of another embodiment of a clip according to the current invention.

FIG. 5 shows an embodiment of the present invention in which the jaws 2 and 3 take a different shape. In this embodiment, the tip of the upper jaw 8 and the tip of the lower jaw 9 extend toward one another such that the pressure from the spring hinge 4 is held on the tips of the jaws 8 and 9 rather than throughout the internal planes of the jaws. This embodiment of the present invention can also hold a flexible elongated medical device in a closed position in the same manner as illustrated by FIG. 4. In yet another embodiment, only one of the jaws has an extension portion extending toward the other jaw.

Figure 6:
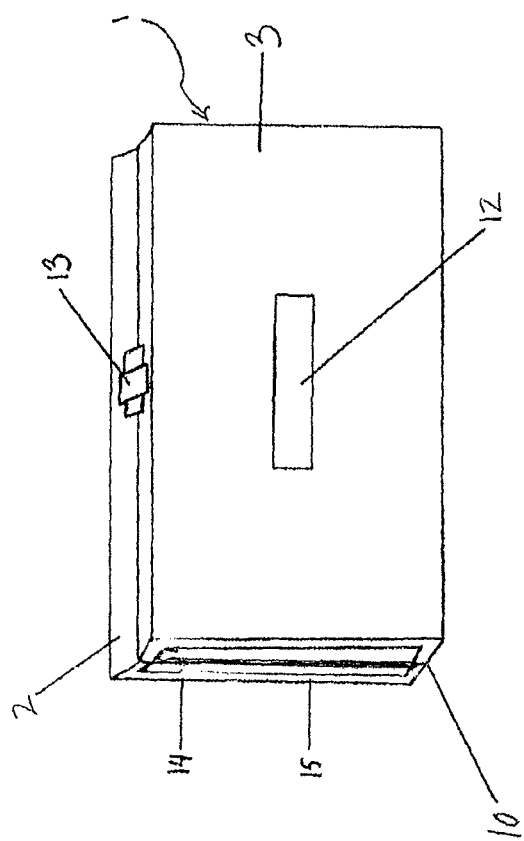
FIG. 6 is a perspective view of yet another embodiment of a clip according to the current invention.
Figure 7:
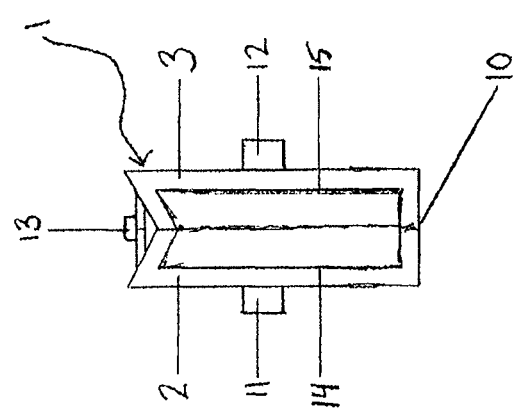
FIG. 7 is a side view of the clip shown in FIG. 6, where the clip is in a closed position.
Figure 8:
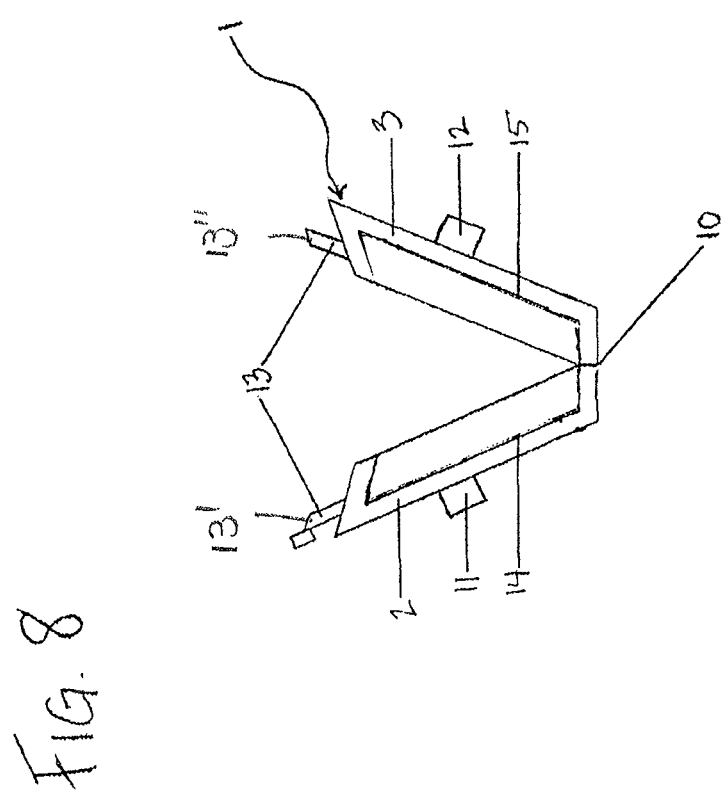
FIG. 8 is a side view of the clip shown in FIG. 6, where the clip is in an open position.
Figure 9:
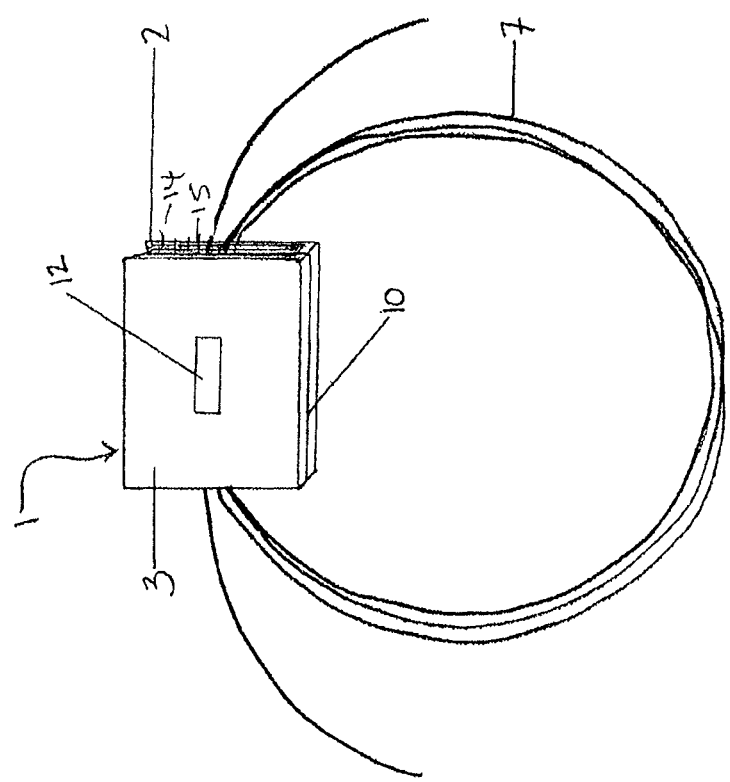
FIG. 9 is a perspective view of the clip shown in FIG. 6 holding a coiled flexible elongated medical device while the clip is in a closed position.

The embodiment of FIGS. 6-9 replaces the spring hinge of prior embodiments with a living hinge 10 that does not provide a spring force. FIG. 6 shows a clip 1 according to this embodiment. The clip 1 features an upper jaw 2 and a lower jaw 3. The jaws 2 and 3 are articulated about a living hinge 10, allowing them to be moved between a closed position, as seen in FIG. 7, and an open position, as seen in FIG. 8. The upper jaw 2 has a holding feature 11 (see FIGS. 7 and 8) and the lower jaw 3 has a holding feature 12 that help the user to control the clip 1 using one hand. As shown in FIGS. 7 and 8, moving the jaws 2 and 3 away from each other causes the clip 1 to open, as illustrated in FIG. 8, and moving the jaws 2 and 3 toward each other causes the clip 1 to close, as illustrated in FIG. 7. Where the upper jaw 2 and the lower jaw 3 meet when the clip 1 is in a closed position is a coupling feature 13 that allows the user to latch the jaws 2 and 3 together when the clip 1 is in a closed position so that the clip 1 can be put down by the user and still retain a flexible elongated medical device 7, as illustrated in FIG. 9. Coupling feature 13 has a first component 13' and a second component 13" that engage to latch. As they engage, second component 13" passes into an opening in first component 13' and engages a surface within that opening. The engagement force of second component 13" with the inside surface of the opening in component 13' as the two components (and the jaws to which they are attached) move with respect to each other transmits a closing force to the jaws. A flexible elongated medical device 7 may be placed between the jaws 2 and 3 through the longitudinal opening when the jaws are open, then the jaws 2 and 3 can be pushed toward each other by the user into the closed position and the coupling feature 13 can be latched by the user so that the jaws 2 and 3 are held together in a closed position thereby holding the flexible elongated medical device 7 without the assistance of the user, as illustrated by FIG. 9. When the user desires to remove the flexible elongated medical device 7 from the clip 1, the user can pick up the clip 1 in the closed position and holding the flexible elongated medical device 7 as illustrated by FIG. 9, unlatch the coupling feature 13, use the holding features 11 and 12 to move the jaws 2 and 3 into the open position, and remove the flexible elongated medical device 7 from the clip 1 through the longitudinal opening.

In embodiments of the invention, one or both of the internal planes of the jaws 2 and 3 have a grasping part 14 and 15, respectively, disposed on the internal planes of the jaws 2 and 3 to hold the flexible elongated medical device 7 in the clip 1 when in a closed position. One or both of such grasping parts can include a flexible material, such as thin metal, flexible plastic, silicone, durometer of 70-80 A, polypropylene, a firm open cell foam, or a silicone foam, to help softly grip the flexible elongated medical device 7 held by the clip 1. This flexible material can be an absorptive material, such as a foam material, cloth, sponge, or gauze. The flexible material may be attached to the inner faces of jaws 2 and 3 with an adhesive. In some embodiments, portions of the flexible material will change shape or deform to accommodate a flexible elongate medical device held between the jaws 2 and 3. In some embodiments, portions of the opposing faces of the flexible material (e.g., at the outer ends of the jaws) may meet even when other portions of the flexible material are holding a flexible elongate medical device, thereby enabling, for example, the ends to the jaws to clip onto an object, such as a sheet on the sterile field, to help with organization during a surgical procedure.

The flexible material may be wet before the clip 1 is used to prevent the clip 1 from sticking to the flexible elongated medical device 7 held by the clip 1 (e.g., due to adherent blood) and so that the clip 1 can moisten the flexible elongated medical device 7 held by the clip 1 by moving the clip 1 with the wet absorptive material over the flexible elongated medical device 7 held by the clip 1. In some optional embodiments the flexible material in the grasping parts 14 and 15 may be made of a PORON Medical® urethane, such as, e.g., soft PORON Medical Slow Recovery urethane. In some optional embodiments, a material with compression set resistance (such as, e.g., PORON Medical urethane) may increase gripping of the flexible elongated medical device. Use of an open cell material may increase gripping of the flexible elongated medical device and may soak up liquid quickly and hold that liquid over an extended period of time to decrease the incidence of sticking to the flexible elongated medical device. In alternative embodiments, a closed cell foam may be used for the flexible material. Use of a lubricious material for the flexible material may also decrease the incidence of sticking to the flexible elongated medical device.

Figure 10:
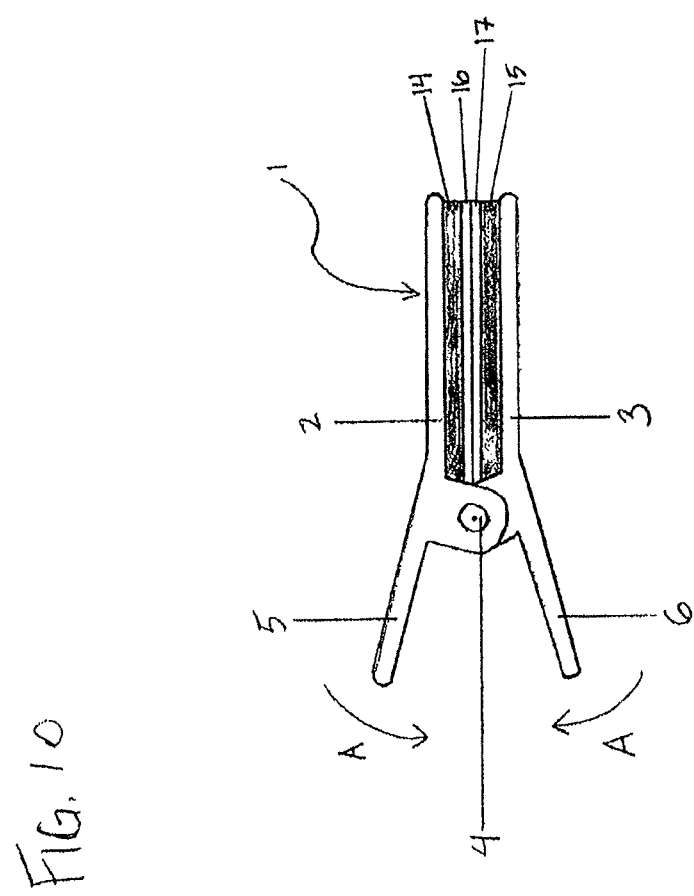
FIG. 10 is a side view of still another embodiment of a clip according to the current invention, where the clip is in a closed position.

In some embodiments, as shown in FIGS. 10 and 11, the grasping parts 14 and 15 may each include an optional layer of cleaning material 16 and 17, respectively, such as gauze, another textile from cotton or polyester, or Telfa, on top of the flexible material to form the contact surfaces that touch the flexible elongated medical device 7 when held by the clip 1 so that the flexible elongated medical device 7 held by the clip 1 can be wiped clean by the user using the clip 1. In embodiments, the internal planes of the jaws of the clip which touch the flexible elongated medical device 7 being held by the clip 1 can optionally be textured, such as by using a molding polymer or a textured textile or foam, to help grip the flexible elongated medical device 7 held by the clip 1, yet that texture cannot have so much grit as to damage the flexible elongated medical device 7 held by the clip 1.

In all embodiments, the pressure placed by the clip 1 on the flexible elongated medical device 7 when in a closed position is between the least pressure needed to hold the flexible elongated medical device in a coiled condition that has the most potential energy when in a coiled condition (i.e., the condition in which the coiled medical device has the highest potential energy due to, e.g., spring forces of the medical device resisting the coiling) and the pressure just less than that which would damage the most fragile flexible elongated medical device when such device is held by the clip such that this flexible elongated medical device is retained in the clip. In one optional embodiment in which the flexible material in the grasping parts 14 and 15 is made of soft PORON Medical Slow Recovery urethane measuring approximately 0.118 inches thick and 2.25 inches wide and a spring hinge with torsion spring is employed, the torsion spring exerts 2.63 inch-pounds of torque with approximately 0.75 inches from the spring's pivot point to the center of the grasping parts 14 and 15 such that approximately 3.5 pounds of force is exerted where a flexible elongated medical device would be held. It is important to note that this is just one of many embodiments that functions to hold this range of flexible elongated medical devices; factors that affect this functionality and dictate the force which the spring or living hinge would need to exert to maintain this functionality include the particular flexible material used, how wide the grasping surfaces are, and the distance from the spring's or living hinge's pivot point to where the flexible elongated medical device held by the clip is gripped.

In all embodiments, the clip 1 is a size that the user can easily operate with only one hand and that does not take too much space when placed on the sterile field or in the bowl filled with saline commonly used during a minimally invasive procedure.

In all embodiments, the jaws 2 and 3 are made of a firm material, which can take various forms. In one embodiment, the jaws 2 and 3 are made of a material that allows for a single-use clip which is to be thrown away after use on one patient, such as a thermoplastic like polyethylene, polypropylene, polystyrene, PVC, or PMMA or an elastometer like silicone; alternative disposable and single-use materials include metal, silicone rubber, nitinol, ABS, polycarbonate, nylon, and/or polyurethane. Alternatively, the jaws 2 and 3 may be made of metal which can be sterilized between uses on different patients, in which case any material covering the grasping part of the internal planes of the jaws (such as the flexible material and optional cleaning material described above), if included in the embodiment and not able to be sterilized for reuse in the same way as the metal, will be single-use such that it can be removed after use on one patient and thrown away so that the clip 1 can be sterilized after use, then new single-use material covering the grasping part of the internal planes of the jaws can be applied onto the grasping part of the internal planes of the jaws 2 and 3 of the sterilized clip 1 for use on a new patient.

In all embodiments, the portion of jaws 2 and 3 held by the user when controlling the jaws 2 and 3 of the clip 1 can take various forms to help the user grip the clip 1. For example, the parts of the clip 1 held by the user can have a ridged surface, a rubber surface, or holes or indentations where the user's fingers can grip the clip 1.

In all embodiments, the clip 1 can have a labeling feature to help the user to identify which flexible elongated medical device 7 is being held by the clip 1. This feature can be on the outward-facing planes of the jaws 2 and 3 and, for example, can be a stick-on type label, a surface adapted to be written on, or a color on the surface of the clip 1 easily visible to the user.

In all embodiments, the part of the jaws 2 and 3 of the clip 1 that hold a flexible elongated medical device 7 when the clip 1 is in a closed position can take various shapes. For example, this part of the clip 1 can be square, rectangular, oval, crescent, or some other shape.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by its claims.

What is claimed is:

1. A clip for holding a flexible elongated medical device, the clip comprising:
    a hinge;
    first and second jaws movable with respect to each other about the hinge from a closed position to an open position, each of the jaws having a contact surface, the contact surface of the first jaw being disposed against the contact surface of the second jaw when the clip is in the closed position and away from the contact surface of the second jaw when the clip is in the open position; and
    flexible material disposed on at least one of the jaws, the flexible material comprising the contact surface, wherein the flexible material comprises PORON Medical® urethane.

2. The clip of claim 1 further comprising a spring biasing the hinge to urge the jaws toward the closed position.

3. The clip of claim 2 wherein a living hinge comprises the hinge and the spring.

4. The clip of claim 1 further comprising first and second handles extending from the first and second jaws, respectively, to move the clip between the closed and open positions.

5. The clip of claim 1 wherein at least one of the jaws has an extension portion extending toward the other jaw, the extension portion contacting the other jaw when the clip is in the closed position.

6. The clip of claim 1 wherein the hinge is a living hinge.

7. The clip of claim 1 further comprising a latch adapted to maintain the clip in the closed position.

8. The clip of claim 7 wherein the latch is further adapted to apply a force to the jaws during actuation of the latch.

9. The clip of claim 1 further comprising a cleaning material disposed over the flexible material, the cleaning material comprising the contact surface.

10. The clip of claim 1 further comprising a textured surface on the flexible material.

11. The clip of claim 1 further comprising a lubricious surface on the flexible material.

12. The clip of claim 1 wherein the flexible material comprises a material which soaks up and holds liquid.

13. The clip of claim 12 wherein the flexible material comprises an open cell foam.

14. The clip of claim 1, wherein the hinge is configured to bias the first and second jaws to the closed position regardless of a position of the clip between the closed position and the open position.

15. The clip of claim 1, further comprising first and second handles extending from the first and second jaws, respectively, to move the clip between the closed and open positions, the hinge being positioned between a side at which the first and second handles are arranged, and an opposite side at which the first and second jaws are arranged.

16. The clip of claim 1, wherein the flexible material is wet.

17. The clip of claim 1, wherein the flexible material is wet and the flexible material is configured to prevent the flexible material sticking to the flexible elongated medical device when the flexible material is wet.

* * * * *